United States Patent [19]

Richards

[11] Patent Number: 4,887,601
[45] Date of Patent: Dec. 19, 1989

[54] ADJUSTABLE SURGICAL STAPLE AND METHOD OF USING THE SAME

[75] Inventor: William D. Richards, Medway, Mass.

[73] Assignee: Ophthalmic Ventures Limited Partnership, Norwood, Mass.

[21] Appl. No.: 118,746

[22] Filed: Nov. 6, 1987

[51] Int. Cl.[4] .................. A61B 17/04; F16B 15/00
[52] U.S. Cl. .................... 606/219; 411/457; 411/920
[58] Field of Search ............ 128/335, 337, 334 R; 411/457, 458, 473, 484, 471, 460, 920; 24/543, 563

[56] References Cited

U.S. PATENT DOCUMENTS

| | | | |
|---|---|---|---|
| 192,121 | 6/1877 | Johnson | 411/457 |
| 1,412,582 | 4/1922 | Panian | 411/473 |
| 1,983,373 | 12/1934 | Horton | 411/457 |
| 2,111,404 | 3/1938 | Pankonin | 411/457 |
| 2,174,708 | 10/1939 | Sears et al. | 227/86 |
| 3,107,390 | 10/1963 | Shelton | 411/457 |
| 3,294,303 | 12/1966 | Anstett | 227/95 |
| 4,014,492 | 3/1977 | Rothfuss | 128/337 |
| 4,043,504 | 8/1977 | Hueil et al. | 227/19 |
| 4,109,844 | 8/1978 | Becht | 227/19 |
| 4,179,057 | 12/1979 | Becht et al. | 227/19 |
| 4,196,836 | 4/1980 | Becht | 128/334 R |
| 4,317,451 | 3/1982 | Cerwin et al. | 128/335 |
| 4,321,002 | 3/1982 | Froehlich | 227/19 |
| 4,399,810 | 8/1983 | Samuels et al. | 128/337 |
| 4,410,125 | 10/1983 | Noiles | 128/334 R |
| 4,428,376 | 1/1984 | Mericle | 411/457 |
| 4,458,387 | 7/1984 | Pearson | 411/457 |
| 4,523,695 | 6/1985 | Braun et al. | 227/19 |
| 4,526,174 | 7/1985 | Froehlich | 128/335 |
| 4,570,623 | 2/1986 | Ellison et al. | 128/334 R |
| 4,619,262 | 10/1986 | Taylor | 128/334 R |
| 4,741,336 | 5/1988 | Failla et al. | 128/334 R |

Primary Examiner—Edward M. Coven
Assistant Examiner—Gary Jackson
Attorney, Agent, or Firm—Schiller, Pandiscio & Kusmer

[57] ABSTRACT

An adjustable surgical staple for use in joining together two pieces of human or animal tissue. The staple has a spine and two legs, with the spine being slotted along its length so as to divide the spine into two separate cross members. Bending the cross members towards or away from one another alters the distance between the leg portions of the staple, thereby allowing precise adjustment of the tension of the joinder between the tissues being joined.

20 Claims, 2 Drawing Sheets

ADJUSTABLE SURGICAL STAPLE AND METHOD OF USING THE SAME

FIELD OF THE INVENTION

This invention relates to surgical fastening devices in general, and more particularly to surgical staples of the sort used to fasten together human or animal tissue.

BACKGROUND OF THE INVENTION

Various surgical stapling devices and staples have been devised for closing wounds or incisions during surgical operations. One of the main reasons for their acceptance as a substitute for conventional suturing is that suturing tends to be very time consuming. A surgeon can frequently close a wound using a surgical stapling device and staples in a minute or two that would otherwise require ten or fifteen minutes to suture. This saving of time is of substantial importance, since it (a) reduces the length of time the patient must be maintained under anesthesia, (b) reduces the surgeon's time, (c) reduces the surgeon's fatigue, and (d) frees up the operating room faster so that it can be used for other surgical procedures.

A number of recent advances in surgical stapling devices and staples have been directed to increasing the variety of surgical procedures in which they can be effectively used. See, for example, the surgical stapling devices and staples described an illustrated in pending U.S. patent application Ser. No. 906,151, filed 9/11/86 by William D. Richards et al. for "Surgical Microstapler", pending U.S. patent application Ser. No. 906,150, filed 9/11/86 by William D. Richards et al. for "Driver for Surgical Microstapler", pending U.S. patent application Ser. No. 944,951, filed 12/22/86 by William D. Richards et al. for "Ophthalmic Stapler" and the pending U.S. patent application filed 11/3/87 by William D. Richards et al. for "Surgical Stapling System". Such surgical stapling devices and staples may be made of such dimensions, and are designed to so minimize stapling trauma to the tissues being joined, that they may be used for delicate surgeries, e.g. ophthalmic surgery or plastic surgery.

However, in some surgeries the need to precisely control the tension of the joinder between the tissues makes even these surgical stapling devices and staples less advantageous than conventional suturing. Such control over the tension of the joinder between the tissues can be particularly important in some types of ophthalmic surgery, e.g. such as where the curvature of the eye must be precisely regulated to minimize optical problems, and some types of plastic surgery, e.g. such as where relative positioning of the tissues must be precisely regulated to minimize cosmetic problems.

OBJECTS OF THE INVENTION

Accordingly, the primary object of the present invention is to provide an adjustable surgical staple which allows the surgeon to adjust the tension of the joinder between the tissues being joined after the staple has been deployed in the tissue.

Another object of the present invention is to provide an adjustable surgical staple which includes novel holding means for enhancing the holding power of the staple in the tissue, whereby the surgeon may manipulate the staple after deployment so as to adjust the tension of the joinder between the tissues being joined without dislodging the staple from the tissue.

Yet another object of the present invention is to provide a novel method for joining together two pieces of tissue using an adjustable surgical staple which allows the surgeon to adjust the tension of the joinder between the tissues being joined after the staple has been deployed in the tissue.

SUMMARY OF THE INVENTION

These and other objects of the present invention are achieved through the use of a novel surgical staple which comprises a spine having first and second opposite ends, and first and second legs, the first leg being attached to the first end of the spine and the second leg being attached to the second end of the spine, wherein the spine is slotted along its length so as to comprise two separate cross members. It is also preferred that each of the staple's legs include a plurality of tiny barbs thereon to enhance the holding power of the staple in the tissue.

During use, the staple is deployed across an incision so that one leg of the staple is disposed on either side of the incision and the spine extends across the incision. The tension of the joinder between the tissues being joined may then be precisely adjusted by manipulating the two cross members toward or away from one another, whereby the spacing between the staple's two legs may be precisely regulated.

BRIEF DESCRIPTION OF THE DRAWINGS

These and other objects and features of the present invention will be more fully described or rendered obvious in the following detailed description of the invention, which is to be considered together with the accompanying drawings wherein like numbers refer to like parts and further wherein.

DETAILED DESCRIPTION OF THE INVENTION

Figure 1:
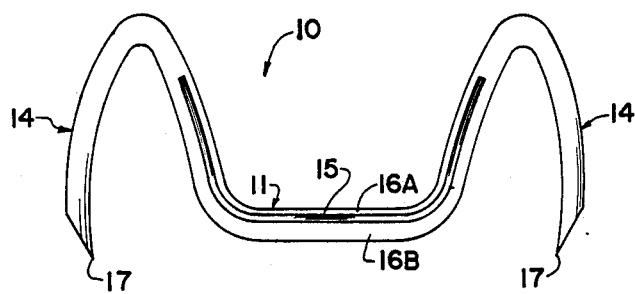
FIG. 1 is a perspective view of an adjustable surgical staple which comprises a first embodiment of the present invention, showing the staple prior to its deployment into tissue.

Looking first at FIG. 1, there is shown a surgical staple 10 which comprises a first embodiment of the present invention. Surgical staple 10 comprises a spine 11 and a pair of identical legs 14. Spine 11 is bisected along its length by a slot 15. Slot 15 divides the spine into two identical, parallel cross members 16A and 16B. Legs 14 are curved so as to extend first upward and then downward from spine 11, and legs 14 terminate in sharp points 17. Preferably slot 15 extends upward along the upwardly-extending portions of legs 14 and terminates prior to reaching the highest points (or "knees") of the legs, as shown in FIG. 1.

Figure 2:
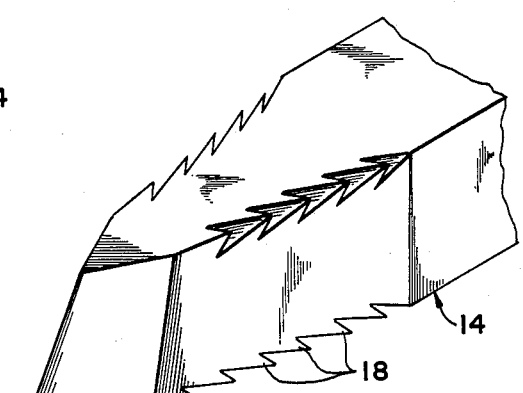
FIG. 2 is an enlarged perspective view of a portion of one leg of the same surgical staple, showing the plurality of tiny barbs formed on each leg of the staple.

Looking next at FIG. 2, a plurality of tiny barbs 18 are preferably (but not necessarily) formed along each of the legs 14 near sharp points 17. Barbs 18 are sufficiently large that they significantly enhance the holding power of the staple when the staple has been deployed in tissue, as will hereinafter be described in further detail, yet are sufficiently small that they will cause minimal trauma to the tissue if and when the staple is subsequently removed.

Figure 3:
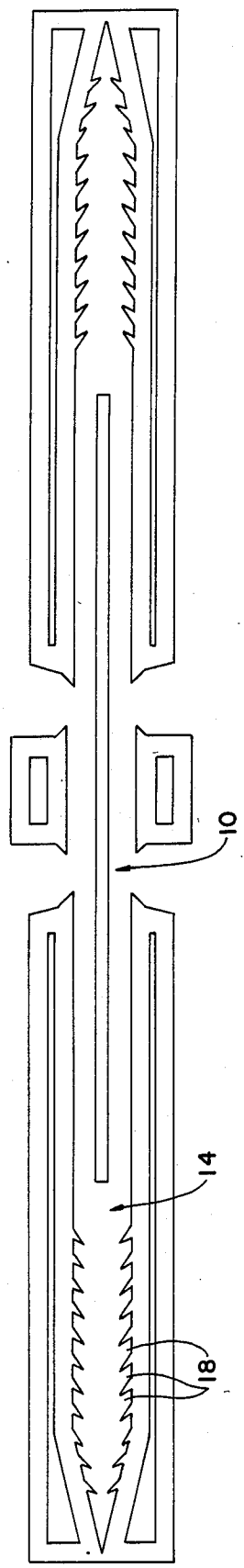
FIG. 3 is a top plan view of the same surgical staple taken during an intermediate step of fabrication (prior to having its two legs bent upward and then downward in the manner shown in FIG. 1), showing the sizing of the staple's tiny barbs relative to the staple as a whole.

FIG. 3 illustrates the sizing of the staple's tiny barbs 18 relative to the staple as a whole; in this connection, it is to be appreciated that FIG. 3 shows the surgical staple during an intermediate stage of fabrication, wherein the staple at this point is a flat strip and its two legs have not yet been bent upward and then downward in the manner shown in FIG. 1.

Figure 4:
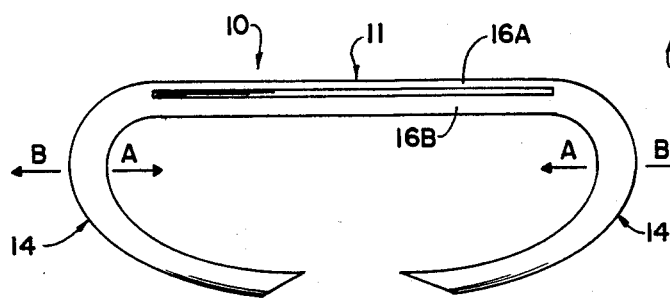
FIG. 4 is a perspective view of the same surgical staple, showing the staple after its deployment into tissue.

Staple 10 (FIG. 1) is generally similar in form to a staple of the type disclosed in the aforementioned U.S. patent application Ser. No. 906,151, the specification and drawings of which are hereby incorporated herein by reference, and is intended to be deployed into tissue in the same general manner as a staple of the type disclosed in the above-identified U.S. patent application Ser. No. 906,151. More specifically, a plurality of staples 10 are created together in the form of a unitary staple strip or magazine of the type disclosed in the above-identified U.S. patent application Ser. No. 906,151, and the staples are intended to be deployed into tissue using a surgical stapler of the type disclosed in U.S. patent application Ser. No. 906,151. It is to be appreciated that once a staple 10 has been deployed in tissue in the foregoing manner it will have assumed the shape shown in FIG. 4, wherein the staple's spine 11 will extend across an incision in the tissue and the two legs 14 are anchored in the tissue on opposite sides of the incision. In the course of deployment, the staple's legs 14 will have been bent downward and inward so that sharp points 17 are oriented towards one another, as shown in FIG. 4. It will be appreciated that those portions of legs 14 which include slot 15 will have been bent so as to extend generally parallel to spine 11, thereby effectively forming flat extensions to the spine, in the manner shown in FIG. 4.

Once staple 10 has been deployed in tissue in the foregoing conventional manner, the surgeon may thereafter utilize the unique characteristics of staple 10 to precisely adjust the tension of the joinder between the tissues being joined. The surgeon does this by manipulating cross members 16A and 16B toward or away from one another, which results in a corresponding adjustment of the spacing between legs 14, and hence a corresponding adjustment of the tension of the joinder between the tissues being joined. More specifically, if the surgeon wishes to tighten the joinder between the tissues, he forces cross members 16A and 16B apart, whereby legs 14 will be moved inward in the direction of the arrows A (see FIG. 4), so that the distance between the legs will decrease and the two pieces of tissue being joined by the staple will be brought closer together. Correspondingly, if the surgeon thereafter wishes to loosen the joinder between the tissues, he forces cross members 16A and 16B together, whereby legs 14 will be eased outward in the direction of the arrows B (see FIG. 4) so that the distance between the legs will increase and the two pieces of tissue being joined by the staple will be eased further apart. Of course, it will be appreciated that the staple shown in FIGS. 1 and 4 can never have its legs further apart than they are when the staple is first set, since at the time of setting the cross members 16A and 16B will extend perfectly parallel to one another and manipulation of the cross members either towards or away from one another can only shorten the distance between the legs. However, it will also be appreciated that once legs 14 have been brought closer together by manipulation of the cross members, they can then be spread apart again by further manipulation of the cross members in the manner previously described.

From the foregoing it will be appreciated that staple 10 must be formed out of a material which is simultaneously strong, bendable, and capable of holding a bent configuration until subjected to a further force adequate to cause it to further bend or unbend, inasmuch as staple 10 must be capable of both holding together tissue and being adjustable through manipulation of its cross members 16A and 16B. Staple 10 must also be formed out of a material which is biocompatible with the tissue it is deployed in. It has been found, or it is believed, that satisfactory staples may be formed out of conventional materials such as 316L stainless steel. Still other materials will be well known to those skilled in the art.

It is also to be appreciated that certain modifications may be made to the preferred embodiment described above without departing from the scope of the present invention.

Thus, for example, the tiny barbs 18 could be omitted from the staple legs and a more conventional staple leg design utilized. However, it is to be appreciated that tiny barbs 18 serve an important function inasmuch as they enhance the holding power of the staple in the tissue, whereby the staple will remain solidly anchored in the tissue even as cross members 16A and 16B are adjusted relative to one another. It is also to be appreciated that tiny barbs 18 simultaneously allow a deployed staple to be deliberately removed at some future date without causing excessive trauma to the joined tissue. The size, shape, and location of the barbs may also be varied.

The present invention could also be practiced with staples that are similar to the one shown in FIG. 1, except that slot 15 is shortened so as to terminate within spine 11 instead of extending upward along the upwardly-extending portions of legs 14.

Figure 5:
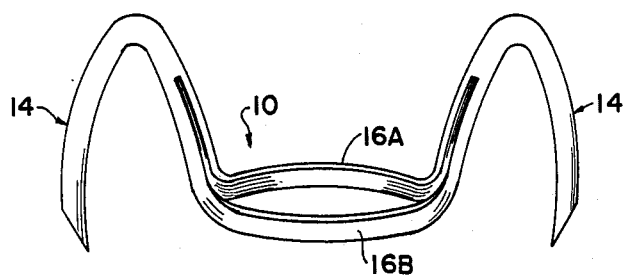
FIG. 5 is a perspective view of an adjustable surgical staple which comprises a second embodiment of the present invention, showing the staple prior to its deployment into tissue.
Figure 6:
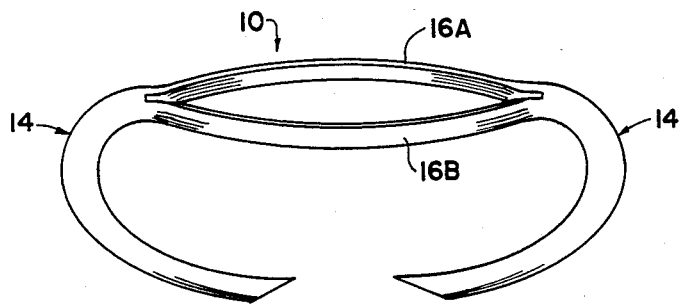
FIG. 6 is a perspective view showing the staple of FIG. 5 after its deployment into tissue.

It is also anticipated that the present invention may be practiced with staples having a shape other than that shown in FIG. 1, e.g. it could be used with a staple having a shape as shown in FIGS. 5 and 6, wherein the staple's cross members are bowed away from one another. This construction has the advantage that the initial spacing between the legs when the staple is deployed can be increased, since the cross members are not yet parallel at the time of deployment. With the staple of FIGS. 5 and 6, legs 14 could be eased outwardly from one another immediately after deployment simply by forcing cross members 16A and 16B towards one another, i.e., by removing the outward bow in each cross member.

Figure 7:
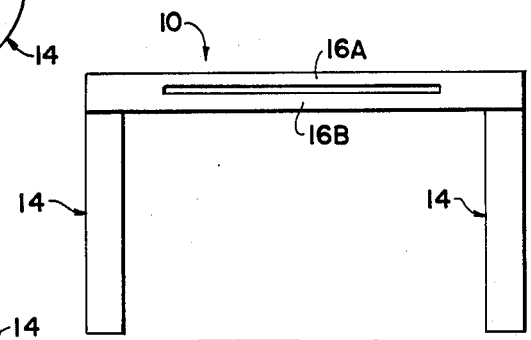
FIG. 7 is a perspective view of an adjustable surgical staple which comprises a third embodiment of the present invention, showing the staple prior to its deployment into tissue.
Figure 8:
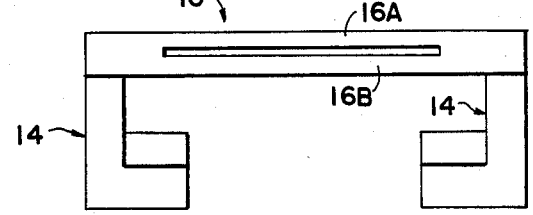
FIG. 8 is a perspective view showing the staple of FIG. 7 after its deployment into tissue.

Alternately, the present invention may be practiced with a conventional, U-shaped staple such as that shown in FIG. 7, wherein the legs 14 are straight and extend at a substantially right angle from the spine. The staple is set in place using an anvil-equipped stapler. FIG. 8 shows the shape of the staple of FIG. 7 after it has been set in place. In this situation, the length of slot 15 in the spine may be relatively short or long, as desired, and the legs of the staple may or may not include tiny barbs as shown in FIGS. 2 and 3.

Still other changes of this type will be obvious to persons skilled in the art and are considered to be within the scope of the present invention.

ADVANTAGES OF THE INVENTION

Numerous advantages are achieved by utilizing the present invention.

First, the present invention provides an adjustable surgical staple which allows the surgeon to precisely adjust the tension of the joinder between the tissues being joined after the staple has been deployed in the tissue.

Second, the present invention provides an adjustable surgical staple which includes novel holding means for enhancing the holding power of the staple in the tissue, whereby the surgeon may manipulate the staple after deployment so to precisely adjust the tension of the joinder between the tissues being joined without dislodging the staple from the tissue.

Third, the present invention provides a novel method for joining together two pieces of tissue using an adjustable surgical staple which allows the surgeon to precisely adjust the tension of the joinder between the tissues being joined after the staple has been deployed in the tissue.

Fourth, the present invention provides a staple whose spine, because it is bisected by a slot, has greater flexibility, smaller size, and nearly the same strength as a conventional staple spine; as a result, the staple may provide less lid irritation when used in ophthalmic surgery, and may allow further manipulation of the staple by the surgeon after deployment without causing the staple to loosen in the tissue.

Fifth, the present invention provides an adjustable surgical staple that may be made in various sizes, depending on its application. By way of example, for ophthalmic purposes, the staple of FIG. 1 might have a length, in its unbent state (i.e., that of FIG. 3), of 0.109 inches.

What is claimed is:

1. An adjustable surgical staple comprising a spine and two curved legs formed integral with opposite ends of said spine, and a slot extending along the length of the spine, said slot extending fully through said spine.

2. An adjustable surgical staple according to claim 1 wherein said slot also extends along a portion of each leg, said slot also extending fully through said legs.

3. An adjustable staple comprising a substantially straight spine means and a pair of arched legs formed integral with the opposite ends of said spine means, and a slot in said spine means extending lengthwise thereof and subdividing said spine means into two mutually space spine sections, said spine sections being deformable when forced toward or away from one another and capable of retaining their deformed shape when the deforming force is removed.

4. An adjustable staple according to claim 3 wherein said slot also extends along a portion of each leg so that each leg has a pair of mutually spaced leg sections that are deformable when forced toward or away from one another and are capable of retaining their deformed shape when the deforming force is removed.

5. An adjustable surgical staple comprising:
(a) a spine having first and second opposite ends;
(b) first and second legs, said first leg being attached to said first end of said spine, and said second leg being attached to said second end of said spine; and
(c) adjustment means for adjusting the spacing between said first and second legs, said adjustment means being disposed between said first and second ends of said spine and comprising two separate, movable cross members separated by a slot, said cross members being formed so as to be readily movable toward and away from one another, whereby manipulation of said cross members toward and away from one another will result in changes in the spacing between said first and second legs.

6. An adjustable surgical staple comprising:
adjustable spine means having first and second opposite ends, and
first and second legs, said first leg being attached to said first end of said spine means, and said second leg being attached to said second end of said spine means, said legs being formed so that when said adjustable surgical staple is driven into tissue, at least a portion of each leg extends toward a corresponding portion of the other leg,
said adjustable spine means comprising two separate cross members separated by a slot, said slot extending completely through said adjustable spine means, and said cross members being formed so as to be readily movable toward and away from on another, whereby manipulation of said cross members toward and away from one another will result in changes in the spacing between said legs.

7. An adjustable surgical staple according to claim 6 wherein each of said legs includes a plurality of tiny barbs thereon, said barbs being large enough that they will enhance the holding power of the staple in tissue and small enough that they will allow a deployed staple to be removed without causing excessive trauma to the joined tissue.

8. An adjustable surgical staple according to claim 6 wherein said slot also extends along a portion of each of said legs, said slot extending completely through said legs.

9. An adjustable surgical staple according to claim 6 wherein said cross members extend parallel to one another prior to manipulation of said cross members toward and away from one another.

10. An adjustable surgical staple according to claim 6 wherein said cross members do not extend parallel to one another prior to manipulation of said cross members toward and away from one another.

11. An adjustable surgical staple according to claim 5 wherein said legs are formed so that when said adjustable surgical staple is driven into tissue, at least a portion of each leg extends substantially parallel to said adjustable spine means.

12. An adjustable surgical staple according to claim 10 wherein said cross members initially bow outward, away from one another, prior to manipulation of said cross members toward and away from one another.

13. A method for attaching together two portions of tissue, said method comprising the steps of:
  (1) providing an adjustable surgical staple, said adjustable surgical staple comprising:
  spine means having first and second opposite ends, and
  first and second legs, said first leg being attached to said first end of said spine, and said second leg being attached to said second end of said spine,
  said spine means being slotted along its length so as to comprise two separate cross members that may be manipulated toward or away from one another so as to change the spacing between said first and second legs,
  (2) deploying said adjustable surgical staple in the two portions of tissues to be joined so that said first leg is disposed in one tissue portion and said second leg is disposed in said second tissue portion; and
  (3) manipulating said cross members toward or away from one another so as to precisely adjust the tension of the joinder formed by said staple between said two tissue portions.

14. A method according to claim 13 wherein each of said legs includes a plurality of tiny barbs thereon, said barbs being large enough that they will enhance the holding power of the staple in tissue and small enough that they will allow a deployed staple to be removed without causing excessive trauma to the joined tissue.

15. A method according to claim 13 wherein a portion of each of said legs is also slotted, said legs being slotted against said spine means so that each leg comprises a pair of opposed mutually spaced sections, and further wherein step (3) is conducted so that the opposed sections of each leg are manipulated with said cross members toward or away from one another to adjacent the tension of the joinder between said two tissue portions.

16. A method according to claim 13 wherein said cross members extend parallel to one another when said staple is deployed in said two tissue portions.

17. A method according to claim 13 wherein said cross members do not extend parallel to one another when said staple is deployed in said two tissue portions.

18. A method according to claim 17 wherein said cross members initially bow outward, away from one another, prior to manipulation of said cross members toward or away from one another.

19. A method according to claim 13 wherein said adjustable surgical staple is deployed in the two portions of tissue so that at least a portion of each leg extends toward a corresponding portion of the other leg.

20. A method according to claim 13 wherein said adjustable surgical staple is deployed in the two portions of tissue so that at least a portion of each leg extends substantially parallel to said spine means.

* * * * *